(12) United States Patent
Madhusudhana et al.

(10) Patent No.: US 11,594,253 B2
(45) Date of Patent: *Feb. 28, 2023

(54) DETECTING LOSS OF ATTENTION DURING PLAYING OF MEDIA CONTENT IN A PERSONAL ELECTRONIC DEVICE

(71) Applicant: MOTOROLA MOBILITY LLC, Chicago, IL (US)

(72) Inventors: Nikhil Ambha Madhusudhana, Chicago, IL (US); Vivek K. Tyagi, Chicago, IL (US); Joseph V. Nasti, Chicago, IL (US)

(73) Assignee: Motorola Mobility LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,892

(22) Filed: Oct. 13, 2021

(65) Prior Publication Data

US 2022/0068310 A1 Mar. 3, 2022

Related U.S. Application Data

(63) Continuation of application No. 16/931,140, filed on Jul. 16, 2020, now Pat. No. 11,164,602.

(51) Int. Cl.
*H04N 9/80* (2006.01)
*G11B 27/00* (2006.01)
(Continued)

(52) U.S. Cl.
CPC .............. *G11B 27/005* (2013.01); *A61B 5/16* (2013.01); *A61B 5/378* (2021.01); *A61B 5/38* (2021.01);
(Continued)

(58) Field of Classification Search
CPC .. A61B 5/16; A61B 5/378; A61B 5/38; A61B 5/742; A61B 2503/12; G11B 27/005; G11B 27/11; G11B 27/34; G11B 27/36
(Continued)

(56) References Cited

U.S. PATENT DOCUMENTS

| 10,382,823 | B2 | 8/2019 | Krishnamoorthy |
| 2011/0078572 | A1 | 3/2011 | Milazzo |
| 2015/0070516 | A1* | 3/2015 | Shoemake ......... H04N 21/4542 348/207.11 |

OTHER PUBLICATIONS

Frank et al., "Sensor-based Identification of Human Stress Levels", 10th IEEE International Workshop on Managing Ubiquitous Communications and Services 2013, San Diego, Mar. 18, 2013.
(Continued)

*Primary Examiner* — Robert Chevalier
(74) *Attorney, Agent, or Firm* — Isidore PLLC

(57) ABSTRACT

A mobile device has at least one media output device for presenting first media content, at least one communication interface that receives signals/data indicative of whether a consumer of the first media content is actively consuming the first media content; and at least one processor executing program code, which enables the mobile device to: during playing of a first media content, receive, via the communication interface, the first data; evaluate, based on a comparison of the first data with comparative data, whether the first data indicates that the consumer is not paying attention to the first media content; and in response to the consumer not paying attention, identify, by the processor, based on a time of receipt of the first data, a first time corresponding to a location within the first media content at which the consumer stopped paying attention during the playback of the first media content.

9 Claims, 11 Drawing Sheets

(51) Int. Cl.
    *G11B 27/11*     (2006.01)
    *G11B 27/36*     (2006.01)
    *G11B 27/34*     (2006.01)
    *A61B 5/00*     (2006.01)
    *A61B 5/16*     (2006.01)
    *A61B 5/38*     (2021.01)
    *A61B 5/378*     (2021.01)

(52) U.S. Cl.
    CPC .............. *A61B 5/742* (2013.01); *G11B 27/11* (2013.01); *G11B 27/34* (2013.01); *G11B 27/36* (2013.01); *A61B 2503/12* (2013.01)

(58) Field of Classification Search
    USPC .......................... 386/241, 239, 248, 278, 326
    See application file for complete search history.

(56) References Cited

OTHER PUBLICATIONS

Li, et al., "A Smart Safety Helmet using IMU and EEG sensors for worker fatigue detection", ieeexplore, ieee.org, document 6952983, 2014 IEEE.

\* cited by examiner

DETECTING LOSS OF ATTENTION DURING PLAYING OF MEDIA CONTENT IN A PERSONAL ELECTRONIC DEVICE

PRIORITY APPLICATION

This application is a continuation of application Ser. No. 16/931,140, filed Jul. 16, 2020, the content of which is fully incorporated herein.

BACKGROUND

1. Technical Field

The present disclosure generally relates to personal electronic devices that can play media content and in particular to mechanisms and methods for responding to loss of attention during play of media content in a personal electronic device.

2. Description of the Related Art

A large number of modern personal electronic devices, such as mobile devices and cell phones, are equipped with speakers and a video display that allow the consumption of media content, including listening to audio media and viewing video media. When listening to audio media or viewing video media, a user's attention may be diverted, causing the user to lose attention or focus and to miss a portion of the media content. A user can lose attention for various reasons, such as hearing someone calling the user's name, seeing someone waving to the user, or by a distraction from an ad posted during viewing of or listening to the media content.

After a user regains attention or focus, the user may realize that he/she has missed part of the audio or video content. In order to view the missed media content, the user would have to rewind the audio or video to the place where the user thinks he/she remembers losing attention and then continue play of the audio or video content. Unfortunately, the user may not remember when during the the viewing of the media content that the user's attention or focus was lost.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
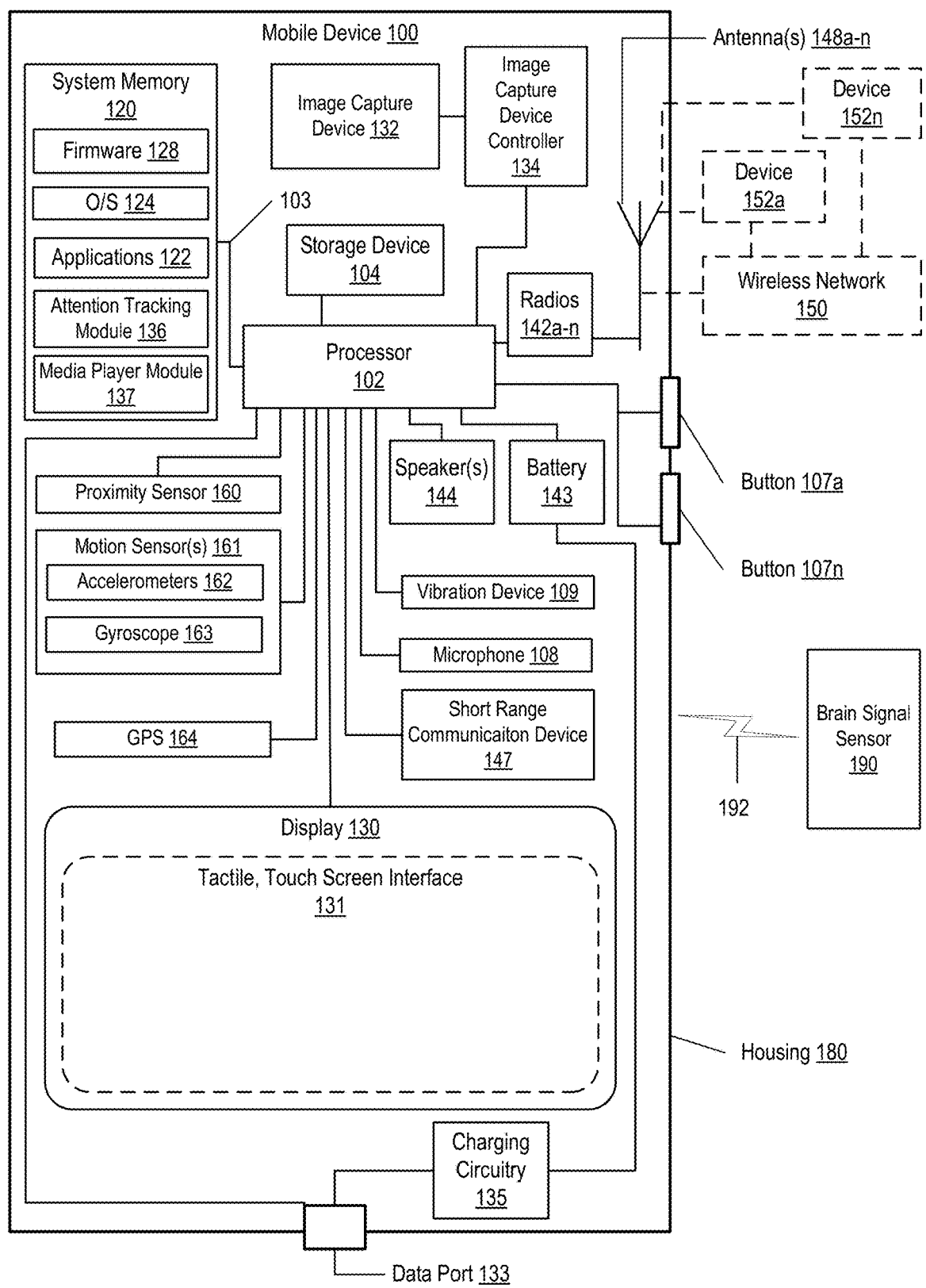
FIG. 1 depicts an example mobile device within which various aspects of the disclosure can be implemented, according to one or more embodiments.

The illustrative embodiments provide a method, a mobile device, and a computer program product for detecting loss of attention during play of media content in a mobile device and responding to the detection of the loss of attention. The method includes receiving, via a processor of a mobile device, first data indicative of whether a consumer of the first media content is actively consuming or not actively consuming first media content. The first data is received during playing of the first media content. The method further includes evaluating, based on a comparison of the first data with comparative or pattern data, whether the first data indicates that the consumer is likely not currently paying attention to the playing of the first media content. The method further includes identifying, based on a time of receipt of the first data indicating that the consumer is not paying attention, a first time within the first media content at which the consumer stopped paying attention during the playing. The method also includes resetting the first media content to a playing location corresponding to the first time and resume playing the media content from the playing location. The playing location can be a specific time when a user has stopped paying attention or can be a more general location such as the beginning of a book chapter or other marked instance within the first media content. The resetting of the content to the playing location can be based on a manual selection of a reset/rewind option presented to the consumer or based on another trigger that does not require manual input, in part dependent on the type of first data received.

According to another embodiment, a mobile device includes a display, a speaker, a memory having stored thereon an attention tracking module. The mobile device further includes at least one processor communicatively coupled to the display, the speaker and the memory. The at least one processor executes program code of the attention tracking module which enables the mobile device to, during playing of a first media content, receive first data indicative of whether a consumer of the first media content is actively consuming or not actively consuming the first media content. The mobile device is further enabled to evaluate, based on a comparison of the first data with comparative or pattern data, whether the first data indicates that the consumer is not currently be paying attention to the playing of the first media content. The mobile device is further enabled to evaluate, based on a time of receipt of the first data indicating that the consumer is not paying attention, a first time within the first media content at which the consumer stopped paying attention during the playing. The mobile device is further enabled to reset a playing location of the first media content corresponding to the first time and resume playing from the playing location. The playing location can be a specific time when a user has stopped paying attention or can be a more general location such as the beginning of a book chapter or other marked instance within the first media content.

According to an additional embodiment, a computer program product includes a computer readable storage device and program code on the computer readable storage device. When executed within a processor associated with an electronic device, the program code enables the device to provide the various functionality presented in the above-described method processes.

The above contains simplifications, generalizations and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and the remaining detailed written description. The above as well as additional objectives, features, and advantages of the present disclosure will become apparent in the following detailed description.

In the following description, specific example embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from the general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various aspects are described which may be aspects for some embodiments but not other embodiments.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the terms first, second, etc. do not denote any order or importance, but rather the terms first, second, etc. are used to distinguish one element from another.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be provided its broadest interpretation given the context in which that term is utilized.

Those of ordinary skill in the art will appreciate that the hardware components and basic configuration depicted in the following figures may vary. For example, the illustrative components within mobile device (100, FIG. 1) are not intended to be exhaustive, but rather are representative to highlight components that can be utilized to implement the present disclosure. For example, other devices/components may be used in addition to, or in place of, the hardware depicted. The depicted example is not meant to imply architectural or other limitations with respect to the presently described embodiments and/or the general disclosure.

Within the descriptions of the different views of the figures, the use of the same reference numerals and/or symbols in different drawings indicates similar or identical items, and similar elements can be provided similar names and reference numerals throughout the figure(s). The specific identifiers/names and reference numerals assigned to the elements are provided solely to aid in the description and are not meant to imply any limitations (structural or functional or otherwise) on the described embodiments.

FIG. 1 depicts example mobile device 100 within which various aspects of the disclosure can be implemented, according to one or more embodiments. Examples of such mobile devices include, but are not limited to, a laptop computer, a notebook computer, a mobile phone, a digital camera, a tablet computer/device, and a smart-watch, etc. Mobile device 100 includes processor 102, which is communicatively coupled to storage device 104, system memory 120, display 130, image capture device controller 134, wireless communication radios 142$a$-$n$, and other components described herein. The components of mobile device 100 are communicatively coupled to each other by a system interconnect 103. Only one of the connections of system interconnect 103 is labeled in FIG. 1.

System memory 120 may be a combination of volatile and non-volatile memory, such as random access memory (RAM) and read-only memory (ROM). System memory 120 can store program code or similar instructions associated with applications 122, an operating system 124, firmware 128, attention tracking module 136 and media player module 137. Although depicted as being separate from firmware 128 and applications 122, attention tracking module 136 and media player module 137 may also be implemented as a portion of firmware 128 or application 122. Processor 102 loads and executes program code stored in system memory 120. Examples of program code that may be loaded and executed by processor 102 include program code associated with applications 122 and program code associated with attention tracking module 136 and media player module 137.

Display 130 can be one of a wide variety of display screens or devices, such as a liquid crystal display (LCD) and an organic light emitting diode (OLED) display. In the illustrated embodiments, display 130 is a touch screen device that includes a tactile, touch screen interface 131 that allows a user to provide tactile/touch input to or control mobile device 100 by touching the display screen.

In one embodiment, image capture device 132 is communicatively coupled to image capture device controller 134, which is communicatively coupled to processor 102. Image capture device 132 can capture images that are within the field of view of image capture device 132.

Radios 142a-n are coupled to antennas 148a-n. Radios 142a-n and antennas 148a-n allow mobile device 100 to communicate wirelessly with external devices 152a-n via wireless network 150. In one embodiment, external devices 152a-n can be radios (i.e., wireless signal transmitters and receivers) located at various cellular communication towers.

Mobile device 100 can further include data port 133, which is connected with processor 102 and charging circuitry 135. Charging circuitry 135 enables external charging of battery 143 via power input through data port 133. Mobile device 100 further includes microphone 108, vibration device 109, one or more speakers 144, and one or more buttons 107a-n. Buttons 107a-n may provide controls for volume, power, and image capture device 132, etc.

Mobile device 100 further includes proximity sensor 160 and motion sensor(s) 161 that are communicatively coupled to processor 102. Proximity sensor 160 can be an infrared (IR) sensor that detects the presence of a nearby object. Motion sensor(s) 161 can include one or more accelerometers 162 and gyroscope 163. Motion sensor(s) 161 can detect movement of mobile device 100 and provide, to processor 102, motion data that indicate the spatial orientation and movement of mobile device 100.

Accelerometers 162 measure linear acceleration of movement of mobile device 100 in multiple axes (X, Y and Z). For example, accelerometers 162 can include three accelerometers, where one accelerometer measures linear acceleration in the X axis, one accelerometer measures linear acceleration in the Y axis, and one accelerometer measures linear acceleration in the Z axis. Gyroscope 163 measures rotation or angular rotational velocity of mobile device 100.

Mobile device 100 further includes additional components, such as global positioning system (GPS) module 164 and short-range communication device 147. GPS module 164 can receive location and time data from GPS satellites. Short-range communication device 147 is a low powered transceiver that can wirelessly communicate with other devices. Short-range communication device 147 can be a variety of devices, such as a near field communication (NFC) device, a Bluetooth device or a wireless fidelity (Wi-Fi) device. Mobile device 100 further includes a housing 180 that contains the component of mobile device 180.

Brain signal sensor 190 is a device that measures brain electrical signal activity detected when brain signal sensor 190 is placed on, near to, or adjacent the scalp. Brain signal sensor 190 can wirelessly communicate with short-range communication device 147 via wireless signal 192. In one embodiment, brain signal sensor 190 can be an electroencephalograph (EEG) that records electrical signal activity of the brain. An EEG includes multiple electrodes placed along the scalp to measure voltage fluctuations resulting from ionic current within the neurons of the brain. The EEG can record the brain's electrical activity over a period of time and process the brain data using various filtering techniques, as will be described later.

Figure 2:
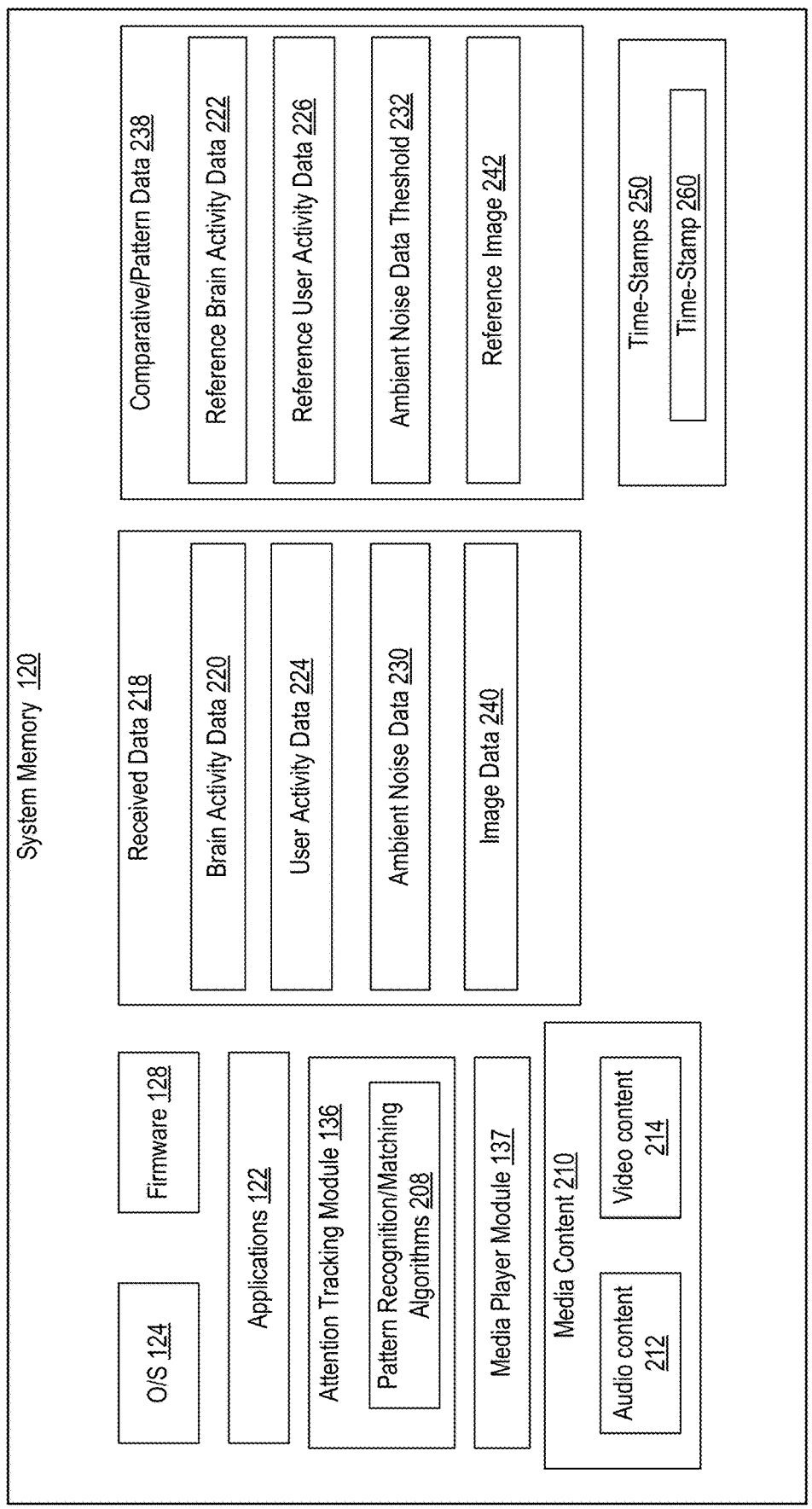
FIG. 2 is a block diagram of example contents of the system memory of the mobile device, which is configured to provide the novel features of the disclosure, according to one or more embodiments.

In the description of each of the following figures, reference is also made to specific components illustrated within the preceding figure(s). With reference now to FIG. 2, one embodiment of example contents of system memory 120 of mobile device 100 is shown. System memory 120 includes data, software, and/or firmware modules, including applications 122, operating system 124, firmware 128, attention tracking module 136, and media player module 137.

Attention tracking module 136 enables tracking of the attention of a user of mobile device 100. Attention tracking module 136 can further evaluate if a user has stopped paying attention or lost focus during play of media content. Attention tracking module 136 includes pattern recognition/matching algorithms 208. Pattern recognition/matching algorithms 208 can learn pattern recognition as mobile device 100 is used over time. Pattern recognition/matching algorithms 208 can be used to identify patterns in data, such if a user has stopped paying attention or has lost focus during play of media content.

In one embodiment, attention tracking module 136 is executed on processor 102 and enables processor 102, and by extension mobile device 100, to perform the processes presented in the flowchart of FIGS. 8A-8B, as will be described below. Media player module 137 enables mobile device 100 to play audio and video media.

According to one aspect of the disclosure, pattern recognition/matching algorithms 208 can include program code that implements an inference engine. An inference engine applies logical rules to a knowledge base or data to deduce new information. An inference engine can be a component of an expert or artificial intelligence system. The inference engine applies logical rules to the data and deduces new knowledge. The process can be iterative as new facts in the data can trigger additional rules in the inference engine. Pattern recognition/matching algorithms 208 can be learned or modified over time based on received data or patterns. Pattern recognition/matching algorithms 208 can recognize and/or match patterns in various types of data.

System memory 120 further includes media content 210. Media content 210 can be a wide variety of media including audio and video media. Media content 210 can include audio content 212, video content 214, and/or audiovisual content. Audio content 212 can include audio books, music, radio and podcasts. Video content can include photos, pictures, videos and movies. System memory 120 also includes received data 218 and comparative/pattern data 238. Comparative/pattern data 238 are pre-determined values of data and patterns that indicate that a user is not paying attention or has lost focus.

Received data 218 includes at least one, and potentially all, of brain activity data 220, user activity data 224, ambient noise data 230, and image data 240. Brain activity data 220 is received from brain signal sensor 190. Brain activity data 220 contains recorded and processed electrical signal data (EEG data) detected/received from a user using brain signal sensor 190. User activity data 224 is received from motion sensor 161. User activity data 224 can indicate that a user of mobile device 100 is at rest or is moving. Ambient noise data 230 is received from microphone 108. Ambient noise data 230 is the noise level of the environment surrounding mobile device 100. In one embodiment, ambient noise data 230 can include data indicating the detection of new individuals who are talking or speaking. The detection/reception by the user of mobile device 100 of the voice or sound of a new individual talking can be distracting to the user. Image data 240 is received from image capture device 132 and is image data captured by image capture device 132.

Comparative/pattern data 238 includes at least one, and potentially all of reference brain activity data 222, reference user activity data 226, ambient noise data threshold 232 and reference image 242. Reference brain activity data 222 is stored, pre-determined EEG data that corresponds to a loss of attention or loss of focus by a user. Reference user activity data 226 is stored, pre-determined data that corresponds to movement or a change in position by a user of mobile device 100. Ambient noise data threshold 232 is a threshold value of noise that when exceeded can correspond to a loss of attention or focus by a user of mobile device 100. In one embodiment, ambient noise data threshold 232 can have a value greater than 70 decibels (dB). Reference image 242 is a stored image. In one embodiment, reference image 242 can correspond to an image of a user of mobile device 100.

System memory 120 further includes time-stamp 250. Time-stamps 250 identify the time that received data 218 is received and corresponds to a time or content location within the media content being played. Time-stamps 250 include at least one time-stamp 260 that is a specific time associated with the playing of media content 210, when a consumer of the media content loses focus or stops paying attention during the playing of media content 210.

Figure 3:
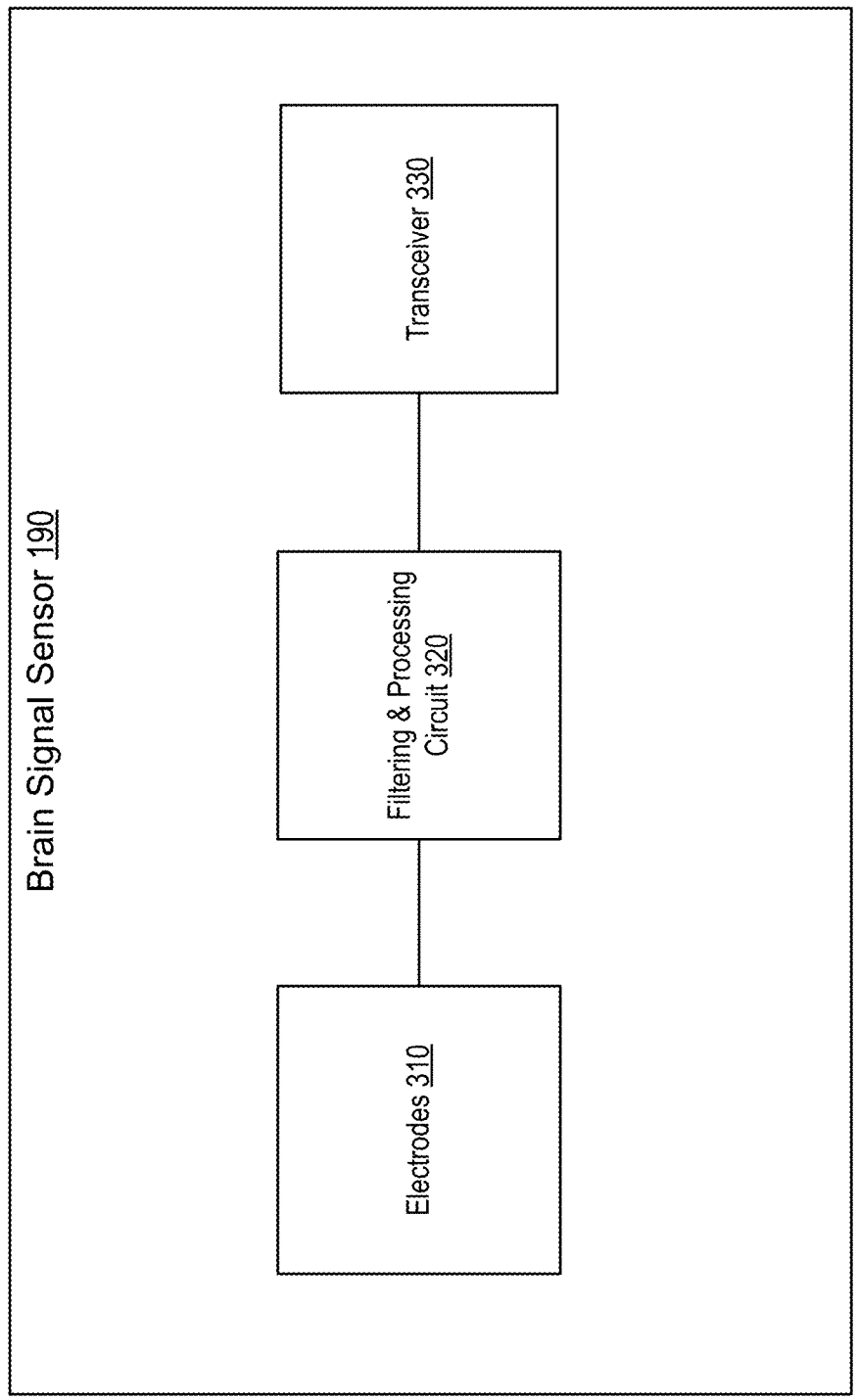
FIG. 3 is a block diagram illustration of a brain sensor, according to one or more embodiments.

FIG. 3 illustrates details of brain signal sensor 190. Brain signal sensor 190 includes electrodes 310, filtering/processing circuitry 320, and transceiver 330. Filtering/processing circuitry 320 is communicatively coupled to electrodes 310 and transceiver 330. Electrodes 310 can contact the scalp of a user and measure/record the brain's electrical activity over a period of time. Filtering/processing circuitry 320 can filter and process the electrical signals received from electrodes 310 and generate brain activity data 220 (FIG. 2). Transceiver 330 enables brain signal sensor 190 to wirelessly send and receive data and instructions from other devices such as mobile device 100. In one embodiment, filtering/processing circuitry 320 can process electrical signals from electrodes 310 in the frequency domain over time to generate neural oscillations (also called "brainwaves"). Neural oscillations or brainwaves are rhythmic or repetitive patterns of neural activity in the brain. Neural tissue can generate oscillatory activity within individual neurons or by interactions between neurons.

Figure 4B:
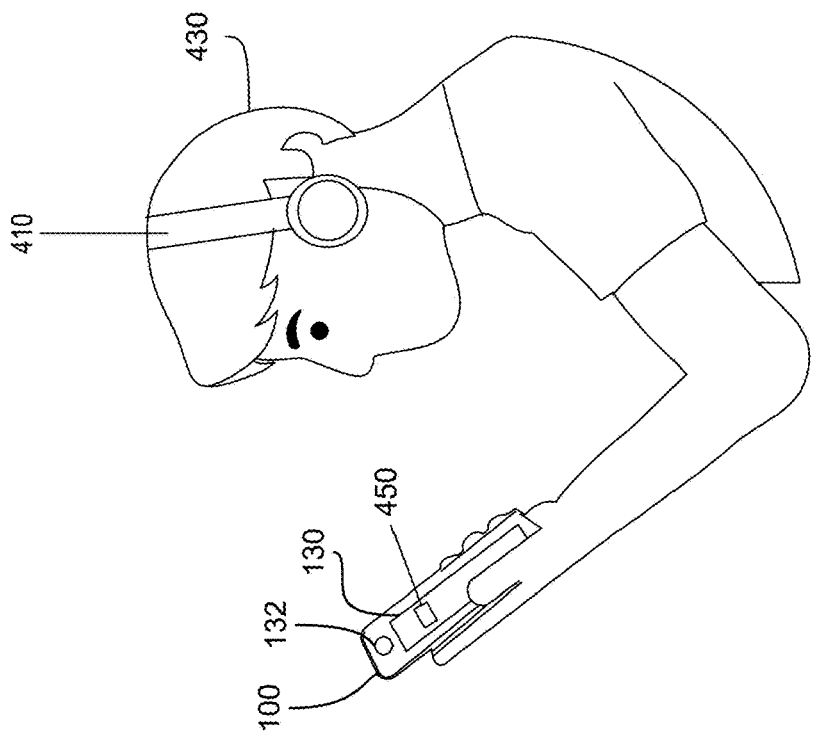
FIG. 4B is an example illustration of a user wearing headphones with a brain signal sensor and using a mobile device, according to one or more embodiments.
Figure 4A:
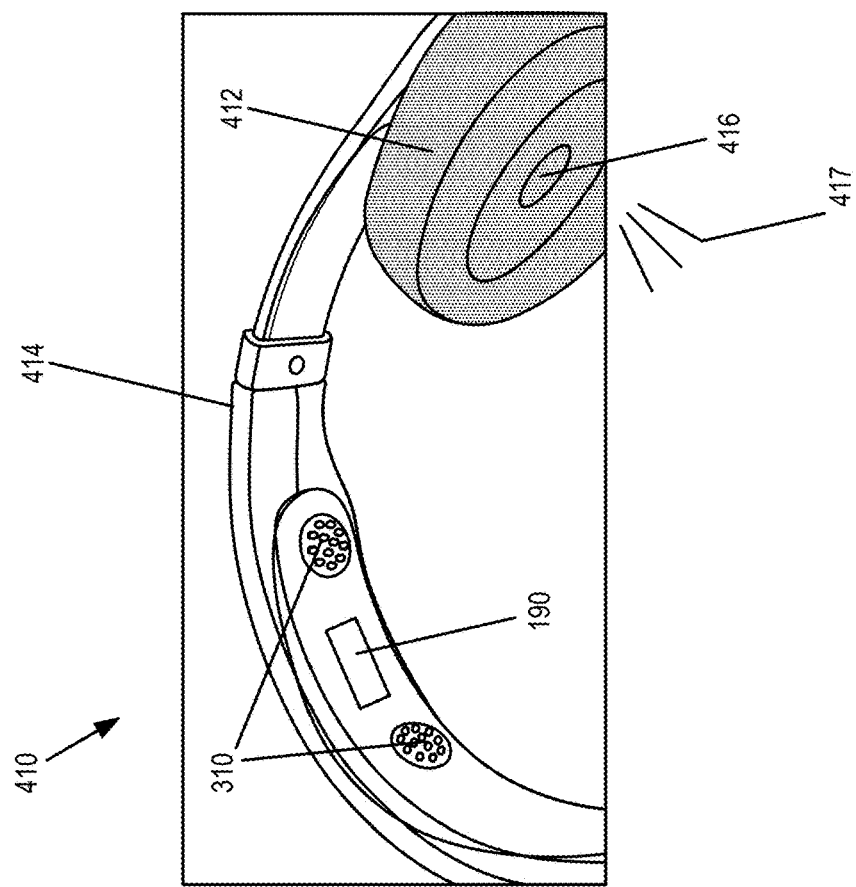
FIG. 4A is an example illustration of headphones that include a brain signal sensor, according to one or more embodiments.

Referring to FIG. 4A, a portion of headphones 410 are shown. Headphones 410 can be worn by a consumer of media and used to listen to audio. Headphones 410 include a pair of ear muffs 412 that are connected by a headband 414. Each ear muff (412) contains a speaker 416. Speaker 416 can produce sounds and audio alerts 417. Headphones 410 can wirelessly receive audio content 212 from mobile device 100 via short range communication device 147 (FIG. 1). In another embodiment, headphones 410 can be in communication with mobile device 100 via a wired connection. Headphones 410 further include brain signal sensor 190. Brain signal sensor 190 is integrated within or attached to headband 414 and/or headphones 410. Electrodes 310 are mounted on an inner surface of headband 414. When headphones 410 are worn by a user, electrodes 310 can contact the scalp of the user. Headphones 410 can wirelessly communicate with mobile device 100 via transceiver 330 (FIG. 3) and short-range communication device 147.

Referring to FIG. 4B, headphones 410 are shown being worn by a user (i.e., media content consumer) 430. The terms "user" and "consumer" will be used interchangeably hereinafter. Consumer 430 can listen to audio content 212 (FIG. 2) playing on mobile device 100 via headphones 410. Consumer 430 can also view video content 214 (FIG. 2) playing on display 130. During play of media content 210 (i.e., audio content 212 and/or video content 214), electrodes 310 (FIG. 3) can measure or record the electrical activity of the brain of consumer 430 over a period of time. Brain signal sensor 190, within headphones 410, can filter and process the electrical signals received from electrodes 310 and transmit brain activity data 220 to mobile device 100 via transceiver 330.

In one embodiment, processor 102, executing attention tracking module 136, receives received data 218 (first data) (i.e., at least one of brain activity data 220, user activity data 224, ambient noise data 230 and image data 240) during playing of media content 210. The received data 218 is indicative of whether a consumer of the media content 210 is actively consuming the media content. Based on pattern recognition and/or a comparison of the received data 218 with comparative/pattern data 238, processor 102 evaluates whether the received data 218 indicates that the consumer is not paying attention to the playing of the media content 210. The comparative/pattern data 238 is at least one of reference brain activity data 222, reference user activity data 226, ambient noise data threshold 232 and reference image 242. According to one aspect, the received data 218 matching the comparative/pattern data 238 is indicative of a high probability that the consumer of the media is not paying attention or has lost focus. In response to determining that the consumer is not paying attention, processor 102 identifies, a first location within the first media content corresponding to the first time at which the consumer stopped paying attention during the playback. The first location is identified based on time-stamp 260 of receipt of the received data 218. Processor 102 rewinds/resets a play location of the media content 210 to continue playing from the first location. In one embodiment, the first location can be at the specific time (i.e., time-stamp 260) when a user has stopped paying attention. In another embodiment, the first location can be a more general location such as the beginning of a book chapter or a movie scene or any other marked instance within the media content. According to one aspect of the disclosure, if the media playing is an audio book, the media location can be rewound/reset to a location that is the beginning of a book chapter that is closest to time-stamp 260 when the user stopped paying attention.

Figure 5:
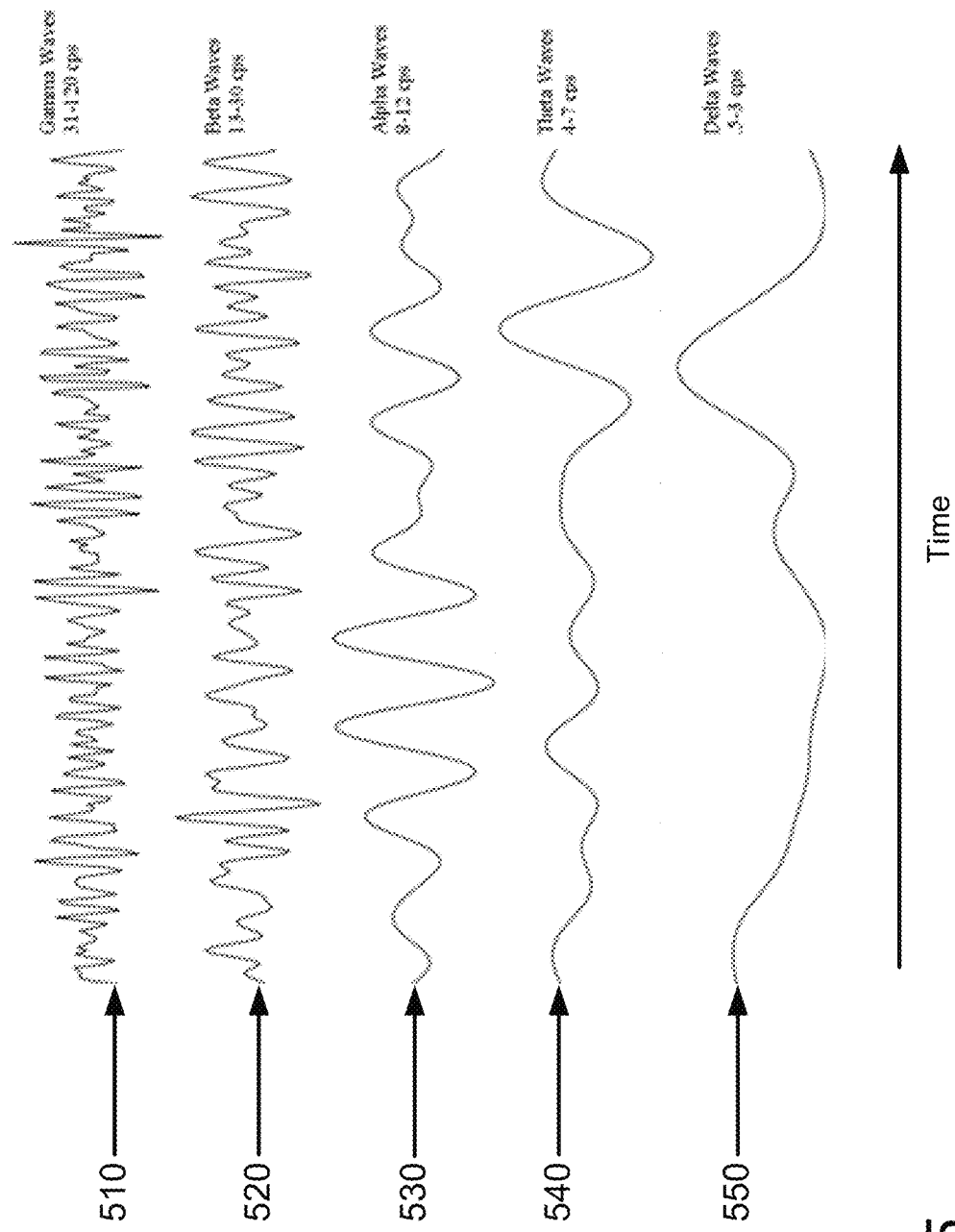
FIG. 5 is an example illustration of various types of electroencephalograph (EEG) brain waves, according to one or more embodiments.

FIG. 5 illustrates various types of EEG brain waves that can be detected from a user over a period of time. The EEG brain waves include gamma waves 510, beta waves 520, alpha waves 530, theta waves 540, and delta waves 550. Gamma waves 510 range from 31 to 120 cycles per second (cps) and are associated with hyper-active brain activity. Beta waves 520 range from 31 to 30 cps and are associated with a brain that is engaged in activities and conversation. Alpha waves 530, range from 8 to 12 cps and are associated with a brain that is relaxed and/or meditating. Theta waves 540 range from 4 to 7 cps and are associated with a brain that is drowsy and/or sleeping with dreams. Delta waves 550 range from 0.5 to 3 cps and are associated with a brain that is in deep sleep without dreams.

According to one aspect of the disclosure, reference brain activity 222 (FIG. 2) can be a ratio of theta waves 540 to beta waves 520 (theta/beta ratio). Increased values of theta waves and reduced values of beta waves have been associated with loss of attention, loss of focus and mind wandering in individuals.

Figure 6A:
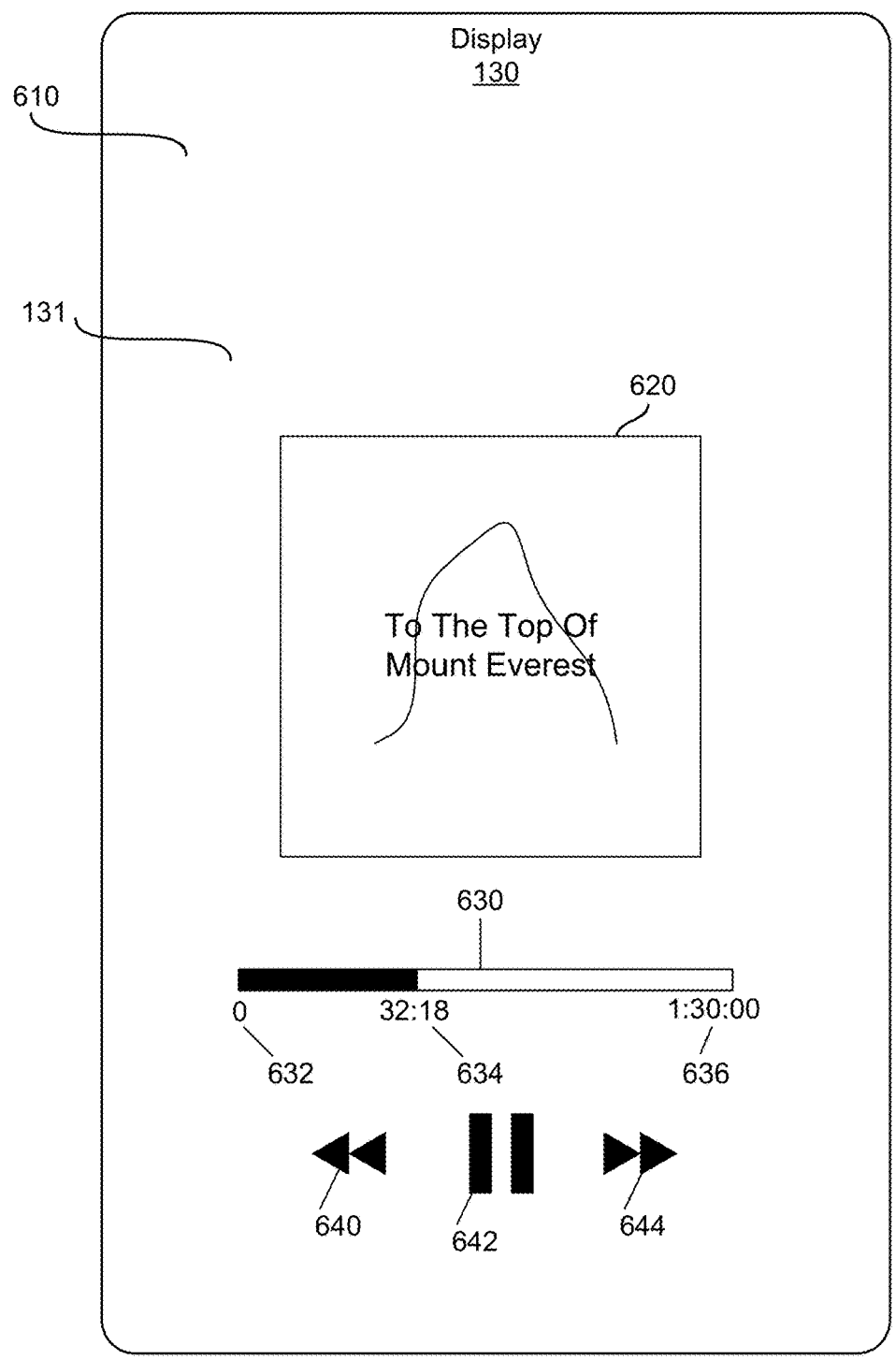
FIG. 6A is an example screen-shot of a display of a mobile device during play of audio media, according to one or more embodiments.

With reference to FIG. 6A, a screen-shot 610 of display 130 during playing of an audio book (i.e., audio content 212 of FIG. 2) is shown. Screen-shot 610 includes a book cover image 620 associated with the audio book and a timeline 630. Timeline 630 indicates the initial time 632, the elapsed time 634 and the total time 636 of audio content 212. Screen-shot 610 further includes rewind icon 640, pause icon 642 and fast forward icon 644. A user listening to the audio content (i.e., a consumer) can use pause icon 642 to pause play of the audio content. Rewind icon 640 enables a consumer of audio content to manually adjust the playback location of the audio content to an earlier point in time. Fast forward icon 644 enables a consumer of audio content to manually skip forward the play location of the audio content 212 to a future point in time.

Figure 6B:
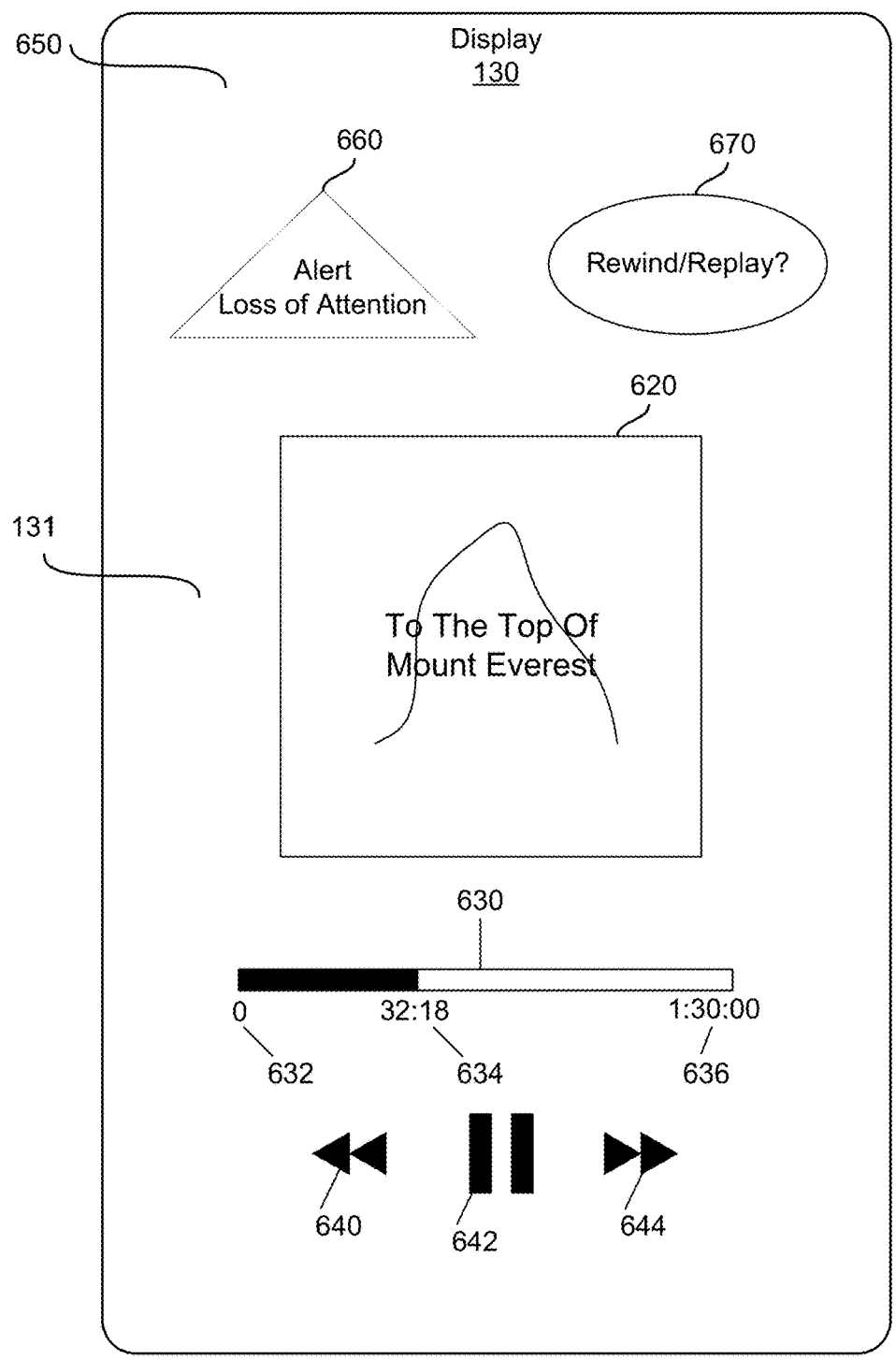
FIG. 6B is an example screen-shot of a display of a mobile device after determining that a consumer of the audio media is not currently paying attention, according to one or more embodiments.

Turning to FIG. 6B, a screen-shot 650 of display 130 is presented after mobile device determines that a consumer of audio content is likely not currently paying attention. Screen-shot 610 includes a "loss of attention" notification or alert 660 and a rewind/replay icon 670. In response to mobile device 100 determining that a user or consumer of media content has stopped paying attention, mobile device 100 presents "loss of attention" notification or alert 660 on display 130 to the user. In an additional embodiment, an audio alert 417 (via speaker 144 or 416) and/or a vibrating alert (via vibration device 109) can be generated by mobile device 100 to notify the user that the user has lost attention. Rewind/replay icon 670, when selected by a user, automatically causes mobile device 100 to first rewind playback of the audio content to the location when the user stopped paying attention or lost focus and then, to continue playback of the audio from time-stamp 260 (FIG. 2) when the user is determined to have stopped paying attention.

Figure 7A:
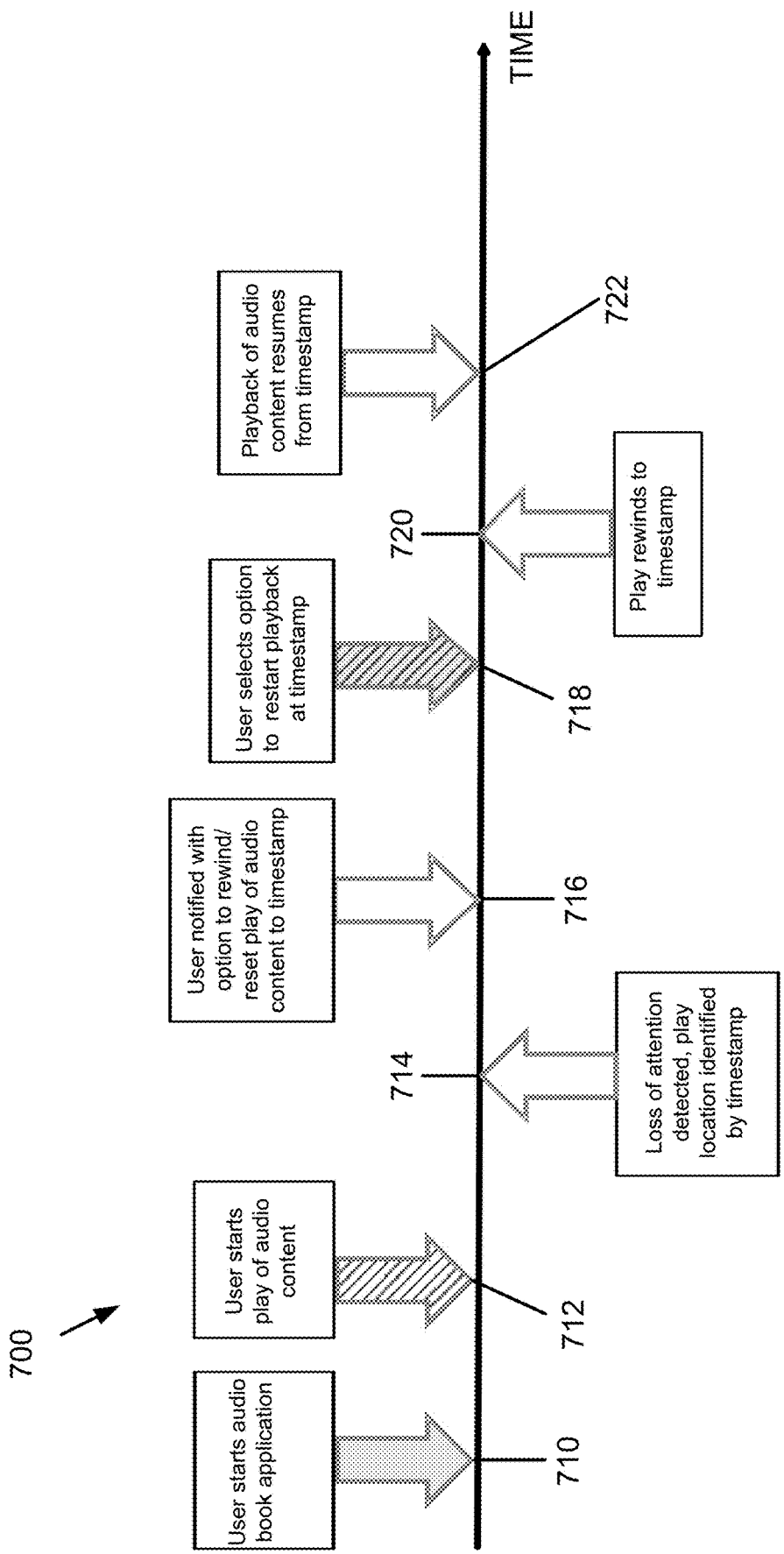
FIG. 7A is an example illustration of a timeline of audio content playing on a mobile device, according to one or more embodiments.

FIG. 7A illustrates one embodiment of a timeline 700 of example audio content 212 playing on mobile device 100. In FIG. 7A, the playback location of the audio content is manually selected for rewinding/resetting. At time 710, a user or consumer of audio content starts an audio book application 122 by selecting an icon on display 130. At time 712, the user selects another icon on display 130 to start play of audio content 212 for consumption/listening via speaker 144 or wireless headphones 410. At time 714, processor 102, executing attention tracking module 136, evaluates, based on pattern recognition and/or a comparison of received data 218 with comparative/pattern data 238, whether the user has stopped paying attention to the audio content 212, and processor 102 determines that the user has lost attention. The received data 218 matching the comparative/pattern data 238 indicates a high probability that the consumer of media is not paying attention or has lost focus. Also at time 714, processor 102 identifies, by time-stamp 260, a time at which the user stopped paying attention during the playing of the audio content 212.

At time 716, processor 102 displays a notification or alert icon 660 on display 130 that indicates that the user has lost attention. Processor 102 also displays a replay/rewind option icon 670 on display 130 that enables user selection to adjust the playback location back to time-stamp 260. The user selects the replay/rewind option icon 670 to restart play of the audio content at the time of time-stamp 260 (time 718). At time 720, processor 102 rewinds/resets a playback location of the audio content to resume playback from time-stamp 260. At time 722, processor 102 resumes or restarts playback of the audio content 212 from time-stamp 260.

Figure 7B:
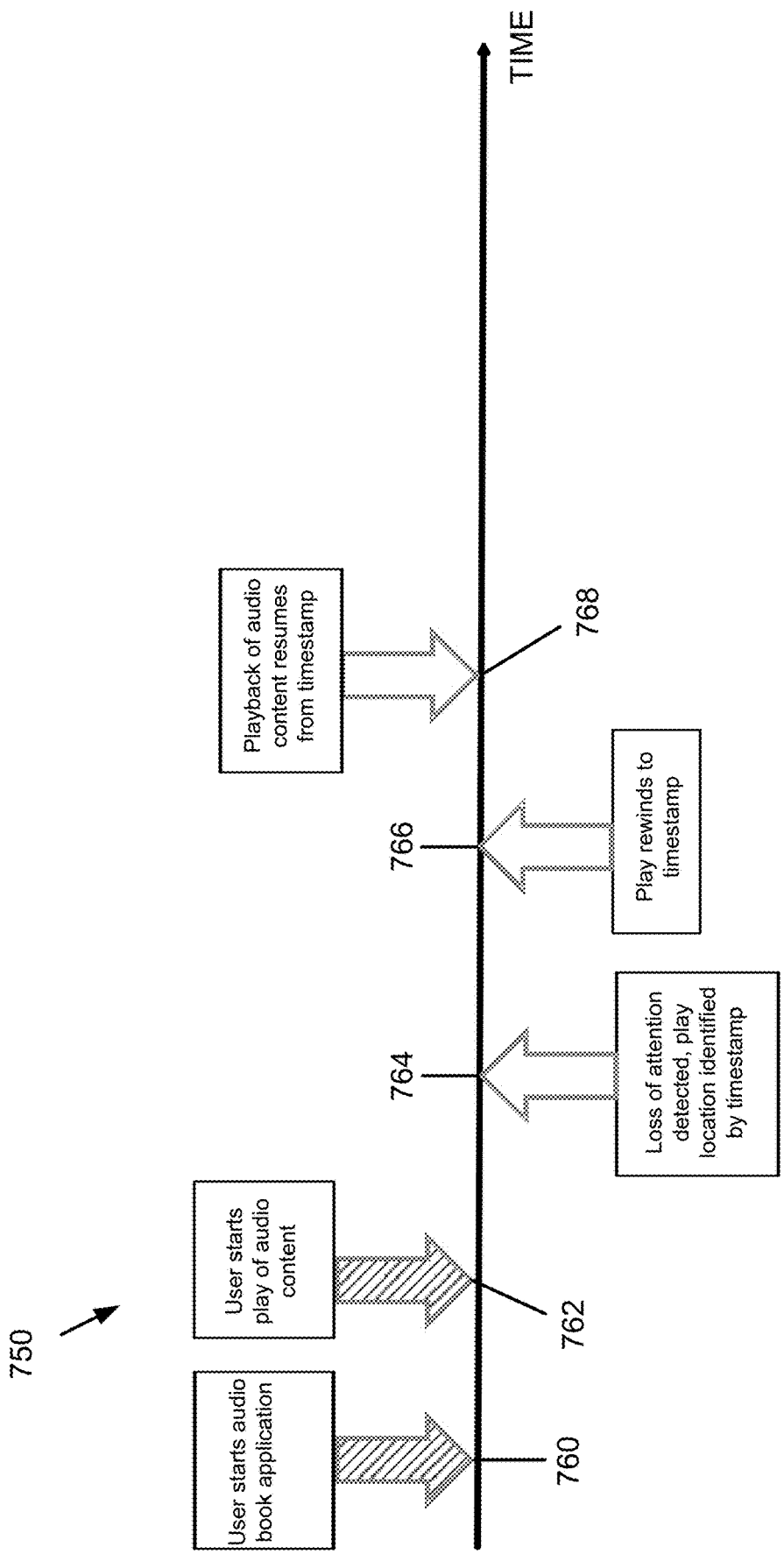
FIG. 7B is an example illustration of another timeline of audio content playing on a mobile device, according to one or more embodiments.

FIG. 7B illustrates another embodiment of a timeline 750 of example audio content 212 playing on mobile device 100. In FIG. 7B, the playback location of the audio content is automatically rewound/reset. At time 760, a user or consumer of audio content starts an audio book application 122 by selecting an icon on display 130. The user selects another icon on display 130 to start play of audio content 212 for consumption/listening via speaker 144 or wireless headphones 410 (time 762). At time 764, processor 102, executing attention tracking module 136, evaluates, based on pattern recognition and/or a comparison of received data 218 with comparative/pattern data 238, whether the user has stopped paying attention to play of the audio content 212, and processor 102 determines that the user has lost focus or is not paying attention. The received data 218 matching the comparative/pattern data 238 indicates a high probability that the consumer of media is not paying attention or has lost focus. Also at time 764, processor 102 identifies, by time-stamp 260, a time at which the user stopped paying attention during play of the audio content 212. At time 766, processor 102 automatically rewinds/resets a playback location of the audio content to continue playback from time-stamp 260. At time 768, processor 102, resumes or restarts playback of the audio content 212 from time-stamp 260. In one embodiment, the playback location can be a more general location such as the beginning of a book chapter within the audio content 212. According to one aspect of the disclosure, if the media playing is an audio book, the playback location can be rewound/reset to a location that is at the beginning of a book chapter that is closest to time-stamp 260 when the user stopped paying attention.

Figure 8A:
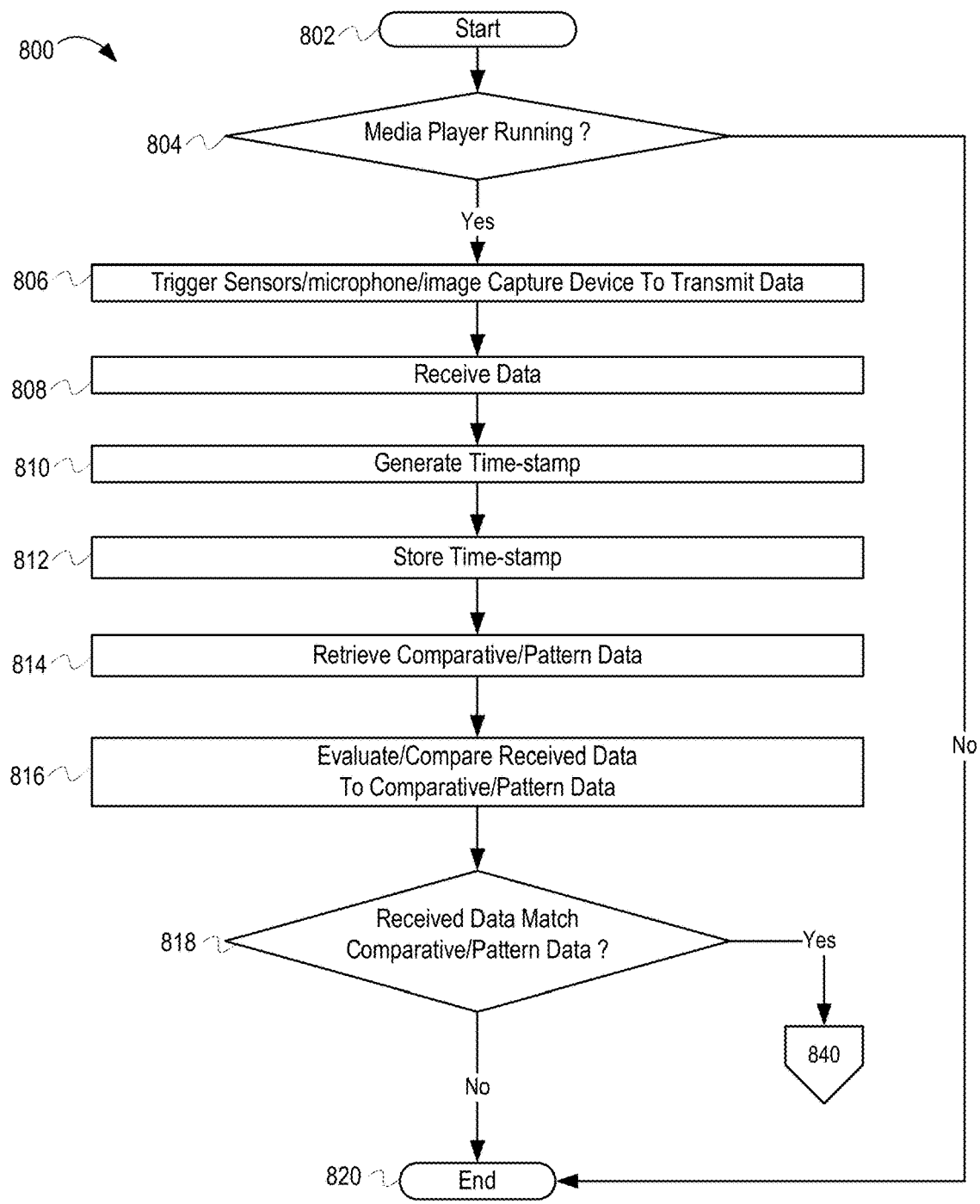
FIGS. 8A-8B depict a flowchart of a method of detecting loss of attention during play of media content in a mobile device and responding to the detection of the loss of attention.
Figure 8B:
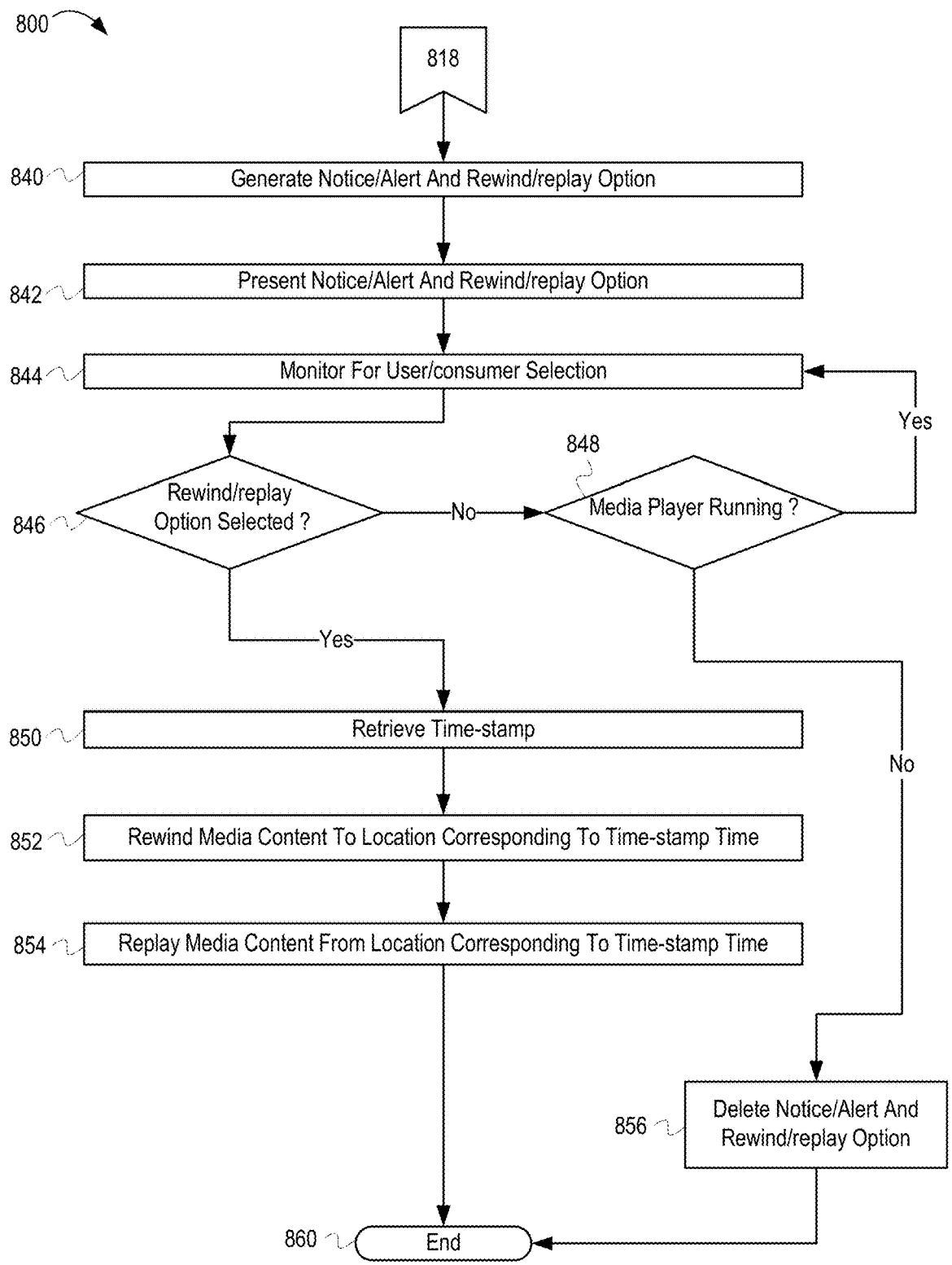

FIGS. 8A-8B depict a method 800 for controlling play of media content in a mobile device. The description of method 800 will be described with reference to the components and examples of FIGS. 1-7B. The operations depicted in FIGS. 8A-8B can be performed by mobile device 100 or other suitable devices. One or more of the processes of the methods described in FIGS. 8A-8B may be performed by a processor (e.g., processor 102) of mobile device 100 executing program code associated with attention tracking module 136.

With specific reference to FIG. 8A, method 800 begins at start block 802. At decision block 804, processor 102 determines if media player module 137 is executing or running. The execution of media player module 137 enables play of media content 210 such as audio and/or video on mobile device 100. In response to media player module 137 not running, method 800 ends at end block 820. In response to media player module 137 running, processor 102 triggers at least one of brain signal sensor 190, motion sensor 161, microphone 108 and image capture device 132 to detect and transmit or send received data 218 (first data) (i.e., at least one of brain activity data 220, user activity data 224, ambient noise data 230, and image data 240) to processor 102 (block 806). Processor 102 receives the received data 218 (i.e., at least one of brain activity data 220, user activity data 224, ambient noise data 230 and image data 240) (block 808). Processor 102 generates time-stamps 250 corresponding to a time when the received data 218 was received (block 810) and stores the time-stamps to system memory 120 (block 812). Time-stamps 250 (FIG. 2) include at least one time-stamp 260 that identifies a time of receipt of the first data and corresponds to a specific time or content location within the media content being played when a user stops paying attention or loses focus.

Processor 102 retrieves comparative/pattern data 238 (i.e., at least one of reference brain data 222, reference user activity data 226, ambient noise data threshold 232, and reference image 242) from system memory 120 (block 814). Comparative/pattern data 238 can contain patterns that processor 102 can evaluate/compare with received data 218. Processor 102 compares the received data 218 to the comparative/pattern data 238 (block 816). In one embodiment, processor 102 can use pattern recognition/matching algorithms 208 within attention tracking module 136 to compare the received data 218 to the comparative/pattern data 238. Processor 102, using pattern recognition/matching algorithms 208, can automatically discover regularities in received data 218 and can classifying the received data into different categories. For example, processor 102, using pattern recognition/matching algorithms 208, can determine if brain activity data 220 has a similar pattern to a ratio of theta waves 540 (FIG. 5) to beta waves 520 (theta/beta ratio) (i.e., reference brain activity 222) and trigger a rewinding of audio content 212.

At decision block 818, processor 102 determines if the received data 218 matches the comparative/pattern data 238 (i.e., at least one of reference brain data 222, reference user activity data 226, ambient noise data threshold 232 and reference image 242). The received data 218 matching the comparative/pattern data 238 indicates a high probability that the consumer of media is not paying attention or has lost focus. In response to determining that the received data 218 does not match the comparative/pattern data 238, method 800 terminates at end block 820.

Turning to FIG. 8B, in response to determining that the received data 218 matches the comparative/pattern data 238, processor 102 generates notice/alert 660 that the user or consumer of media is not paying attention, and processor 102 generates rewind/replay option icon 670 (block 840). Processor 102 presents the notice/alert 660 and rewind/replay option icon 670 on display 130 (block 842). In one embodiment, notice/alert 660 can additionally include an audio alert via speaker 144 and/or a vibrating alert via vibration device 109. Rewind/replay option icon 670 allows a consumer of media to manually, verbally (or otherwise) trigger adjusting of the playback location of media content 210.

With the manual trigger embodiment, processor 102 monitors touch screen interface 131 for entry of the user/consumer selection (block 844). At decision block 846, processor 102 determines if the user/consumer has selected rewind/replay option icon 670. In response to the user/consumer not selecting rewind/replay option icon 670, processor 102 determines if the media player (i.e., media player module 137) is playing (decision block 848). In response to the media player not playing, processor 102 deletes the notice/alert 660 and rewind/replay option icon 670 on display 130 (block 856). Method 800 then ends at end block 860. In response to the media player playing, processor 102 continues to monitor touch screen interface 131 for entry of the user/consumer selection at block 844.

In response to the user/consumer selecting rewind/replay option icon 670, processor 102 retrieves time-stamp 260 (block 850). Processor 102 rewinds/resets media content 210 to the time (or location corresponding to the time) of time-stamp 260 (block 852) and resumes playback of media content 210 from the specific time or playback location corresponding to time-stamp 260 (block 854). Method 800 then terminates at end block 860. In one embodiment, the playback location can be a more general location such as the beginning of a book chapter within the audio content 212.

According to one aspect of the disclosure, if the media playing is an audio book, the playback location can be rewound/reset to a location that is at the beginning of the book chapter that is closest to time-stamp 260 when the user stopped paying attention.

According to one aspect of the disclosure, blocks 840-848 of method 800 can be optional. In one embodiment, blocks 840-848 of method 800 can be omitted. After determining that the received data 218 matches the comparative/pattern data 238, at decision block 818 (FIG. 8A), processor 102 can automatically retrieve time-stamp 260 (block 850), rewind/reset media content 210 to the time of time-stamp 260 (block 852), and resume playback of media content 210 from time-stamp 250 (block 854).

In the above-described methods of FIGS. 8A-B, one or more of the method processes may be embodied in a computer readable device containing computer readable code such that operations are performed when the computer readable code is executed on a computing device. In some implementations, certain operations of the methods may be combined, performed simultaneously, in a different order, or omitted, without deviating from the scope of the disclosure. Further, additional operations may be performed, including operations described in other methods. Thus, while the method operations are described and illustrated in a particular sequence, use of a specific sequence or operations is not meant to imply any limitations on the disclosure. Changes may be made with regards to the sequence of operations without departing from the spirit or scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object-oriented programming language, without limitation. These computer program instructions may be provided to a processor of a general-purpose computer, special-purpose computer, or other programmable data processing apparatus to produce a machine that performs the method for implementing the functions/acts specified in the flowchart and/or block diagram block or blocks. The methods are implemented when the instructions are executed via the processor of the computer or other programmable data processing apparatus.

As will be further appreciated, the processes in embodiments of the present disclosure may be implemented using any combination of software, firmware, or hardware. Accordingly, aspects of the present disclosure may take the form of an entirely hardware embodiment or an embodiment combining software (including firmware, resident software, micro-code, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device can include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage device may be any tangible medium that can contain, or store a program for use by or in connection with an instruction execution system, apparatus, or device.

Where utilized herein, the terms "tangible" and "non-transitory" are intended to describe a computer-readable storage medium (or "memory") excluding propagating electromagnetic signals; but are not intended to otherwise limit the type of physical computer-readable storage device that is encompassed by the phrase "computer-readable medium" or memory. For instance, the terms "non-transitory computer readable medium" or "tangible memory" are intended to encompass types of storage devices that do not necessarily store information permanently, including, for example, RAM. Program instructions and data stored on a tangible computer-accessible storage medium in non-transitory form may afterwards be transmitted by transmission media or signals such as electrical, electromagnetic, or digital signals, which may be conveyed via a communication medium such as a network and/or a wireless link.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

As used herein, the term "or" is inclusive unless otherwise explicitly noted. Thus, the phrase "at least one of A, B, or C" is satisfied by any element from the set {A, B, C} or any combination thereof, including multiples of any element.

While the disclosure has been described with reference to example embodiments, it will be understood by those skilled in the art that various changes may be made and equivalents may be substituted for elements thereof without departing from the scope of the disclosure. In addition, many modifications may be made to adapt a particular system, device, or component thereof to the teachings of the disclosure without departing from the scope thereof. Therefore, it is intended that the disclosure not be limited to the particular embodiments disclosed for carrying out this disclosure, but that the disclosure will include all embodiments falling within the scope of the appended claims.

What is claimed is:

1. A mobile device comprising:
   at least one media output device from among a display that provides video output and a speaker the provides audio output, the media output device for presenting first media content;
   a memory having stored thereon an attention tracking module;
   at least one communication interface that receives signals/data indicative of whether a consumer of the first media content is actively consuming or not actively consuming the first media content; and
   at least one processor communicatively coupled to the at least one media output device, the memory, and the at least one communication interface, the at least one processor executing program code of the attention tracking module which enables the mobile device to:
      during playing of a first media content, receive, via the communication interface, the first data;
      evaluate, based on a comparison by the processor of the first data with comparative data, whether the first data indicates that the consumer is not paying attention to the playback of the first media content; and
      in response to the first data indicating that the consumer is not paying attention, identify, by the processor, based on a time of receipt of the first data, a first time corresponding to a location within the first media content at which the consumer stopped paying attention during the playback of the first media content.

2. The mobile device of claim 1, wherein the processor is further enabled to:
   reset a playback location of the first media content to the first time in order to resume playback from the first time.

3. The mobile device of claim 1, wherein the first data comprises at least one of brain activity data, user activity data, ambient noise data and reference image data that is used in the comparison to the comparative data, the comparative data comprising at least one of reference brain activity data, reference user activity data, ambient noise threshold, and a reference image.

4. The mobile device of claim 1, wherein the processor is communicatively coupled to a brain sensor via the communication interface, the received first data comprises brain activity data, and the comparative data is reference brain activity data, the processor further enabled to:
   during playback of the first media content, receive first brain activity data from the brain sensor via the communication interface;
   retrieve the reference brain activity data from a memory, the reference brain activity data corresponding to a loss of attention by the consumer;
   compare the first brain activity data to the reference brain activity data;
   determine if a result of the comparison of the first brain activity data to the reference brain activity data indicates that the consumer is likely not currently paying attention to the playback of the first media content; and
   in response to the result of the comparison indicating that the consumer is likely not currently paying attention, adjust the playback location of the first media content to account for a time of the change in the brain activity data.

5. The mobile device of claim 4, wherein to adjust the playback location comprises the processor being further enabled to:
   generate a first time-stamp corresponding to when the first brain activity data was received;
   rewind the first media content to the first time-stamp; and
   resume playback of the first media content from the first time-stamp.

6. The mobile device of claim 4, wherein the processor is further enabled to:
   generate a notification that the consumer is not paying attention;

present the notification on the mobile device along with a replay/rewind option for consumer selection to trigger the adjusting of the playback location;

monitor for entry of the consumer selection within a preset period of time after presenting the notification; and trigger the adjusting of the playback location only in response to receiving the consumer selection within the preset time period after the notification.

7. The mobile device of claim 1, wherein the processor is communicatively coupled to a motion sensor, the received first data comprises user activity data, and the comparative data comprises reference user activity data, the processor further enabled to:

during playback of the first media content, receive the first user activity data from the motion sensor;

retrieve the reference user activity data from a memory, the reference user activity data corresponding to a loss of attention by the consumer;

compare the first user activity data to the reference user activity data;

determine if a result of the comparison of the first user activity data to the reference user activity data indicates that the consumer is likely not currently paying attention to the playback of the first media content; and in response to the result of the comparison indicating that the consumer is likely not currently paying attention, adjust the playback location of the first media content to account for the change in the user activity data.

8. The mobile device of claim 1, wherein the processor is communicatively coupled to a microphone, the received first data comprises ambient noise data, and the comparative data comprises an ambient noise data threshold, the processor further enabled to:

during playback of the first media content, receive first ambient noise data from the microphone;

retrieve the ambient noise data threshold from the memory;

determine if the first ambient noise data is greater than the ambient noise data threshold, the first ambient noise data being greater than the ambient noise data threshold indicating that the consumer is likely not currently paying attention to the playback of the first media content; and in response to the first ambient noise data being greater than the ambient noise data threshold, pause playing the first media content until the first ambient noise data is less than the ambient noise threshold.

9. The mobile device of claim 1, wherein the processor is communicatively coupled to an image capture device, the received first data comprises image data and the comparative data is a reference image, the processor further enabled to:

during playback of the first media content, receive the first image data from the image capture device;

retrieve a reference image from a memory;

determine if the first image data matches the reference image, the first image data not matching the reference image indicating that the consumer is likely not currently paying attention to the playback of the first media content;

in response to the first image data not matching the reference image, generate a notification that the consumer is not paying attention; and present the notification on the mobile device along with a replay/rewind option for consumer selection to trigger the adjusting of the playback location.

* * * * *